United States Patent [19]

Azzam

[11] Patent Number: 4,725,145
[45] Date of Patent: Feb. 16, 1988

[54] PHOTODETECTOR ARRANGEMENT FOR MEASURING THE STATE OF POLARIZATION OF LIGHT

[75] Inventor: Rasheed M. A. Azzam, New Orleans, La.

[73] Assignee: Research Corporation, New York, N.Y.

[21] Appl. No.: 822,354

[22] Filed: Jan. 24, 1986

Related U.S. Application Data

[63] Continuation-in-part of Ser. No. 747,611, Jun. 21, 1985, Pat. No. 4,681,450.

[51] Int. Cl.$^4$ ................................. G01J 4/02
[52] U.S. Cl. ................. 356/367; 250/225; 356/369
[58] Field of Search ............ 356/351, 367, 369; 250/225

[56] References Cited

U.S. PATENT DOCUMENTS

3,506,835  4/1970  Foster ............... 356/351 X

Primary Examiner—Davis L. Willis
Assistant Examiner—Matthew W. Koren
Attorney, Agent, or Firm—Scully, Scott, Murphy & Presser

[57] ABSTRACT

An apparatus and method for the measurement of at least one parameter of the state of polarization of a light beam is described. The apparatus includes only a photodetector and no other optical elements. The detector surface is partially specularly reflecting and intercepts the light beam at an oblique angle of incidence. The absorbed fraction of incident radiation produces a corresponding electrical output signal that is detected and from which the at least one parameter of the state of polarization can be determined. The detector may also be rotated to modulate the electrical output signal to determine the elliptic polarization of light except for handedness. A two detector ellipsometer is disclosed wherein light reflected from one detector is absorbed by the second detector and the entire system is rotated.

42 Claims, 6 Drawing Figures

PHOTODETECTOR ARRANGEMENT FOR MEASURING THE STATE OF POLARIZATION OF LIGHT

CROSS-REFERENCE TO RELATED APPLICATIONS

This application is a continuation-in-part of co-pending application Ser. No. 747,611, filed June 21, 1985, now U.S. Pat. No. 4,681,450.

BACKGROUND OF THE INVENTION

1. Field of the Invention

The present invention relates generally to a relatively simple photopolarimeter and method for measuring the state of polarization of a light beam, and more particularly pertains to a unique and simple photopolarimeter and method for measuring at least one parameter defining the state of polarization of a light beam which does not require any of the usual prior art polarizing elements such as wave retarders and polarizers.

2. Discussion of the Prior Art

Many photopolarimeters have been proposed and built to measure the state of polarization of light. See, for example, R. M. A. Azzam and D. L. Coffeen, *Optical Polarimetry Vol.* 112 of Proc. Soc. Photo-Opt. Intrum. Eng. (SPIE, Bellingham Wash., 1977). Generally, the polarimeters employ a sequence of polarizing optical elements such as wave retarders and linear polarizers followed by a photodetector. Polarization sensitivity of photodetectors is considered an annoyance and a possible source of error to be eliminated.

Prior art ellipsometers also employ a sequence of polarizing optical elements followed by a photodetector to measure the polarization state of incident light. U.S. Pat. No. 4,053,232 discloses a rotating ellipsometer wherein the light beam is passed through a polarizer before being reflected from a sample surface. The reflected beam is passed through an encoder, a compensator, and an analyzer before being incident on a photodetector.

SUMMARY OF THE INVENTION

In accordance with the teachings herein, the present invention is directed to a photopolarimeter and method which introduces a new polarimetric concept, that of combining, or integrating, the polarization analysis and photodetection functions in the same components. The apparatus of the present invention includes at least one polarization sensitive photodetector having a partially specularly reflecting surface on which the light beam is incident. The polarization sensitive photodetector produces an electrical output signal having a magnitude proportional to the radiation absorbed by the photodetector.

One photopolarimeter using the new polarmetric concept is disclosed in the applicant's copending application Ser. No. 747,611, filed June 21, 1985, the entire specification of which is herein incorporated by reference. In that application, a light beam is incident on a first photodetector having a partially specularly reflecting surface at an oblique angle with a first plane of incidence, and is partially reflected therefrom. The first photodetector produces a first electrical output signal having a magnitude proportional to the radiation absorbed thereby. The light beam is then subsequently reflected and absorbed by second and third photodetectors also having partially specularly reflecting surfaces which are positioned such that the light beam is incident thereon at an oblique angle at different planes of incidence, that are different from the first plane of incidence. The second and third photodetectors also produce output signals proportional to the radiation absorbed thereby. The fourth photodetector is totally absorbing and produces a fourth electrical output signal proportional to the radiation absorbed.

In another embodiment disclosed in the present invention, an ellipsometer is provided which includes a photodetector having a partially specularly reflecting surface on which the light beam is incident at an oblique angle and which produces an electrical output signal proportional to the radiation absorbed. Means is provided coupled to the photodetector for rotating the photodetector around an axis defined by the incident light beam to modulate the electrical output signal. An auxillary photodetector that intercepts the light beam reflected from the specularly reflecting photodetector may be provided to generate a timing pulse for angular encoding of the modulated output signals.

A further embodiment includes two photodetectors wherein the first detector has a partially specularly reflecting detector surface and the second detector absorbs at least a portion of the light reflected from the first photodetector. In yet another embodiment, the first and second photodetectors are rotated as a unit to present a second plane of incidence for each photodetector. The electrical signals produced by the photodetectors at each of the planes of incidence are processed to determine the elliptic state of polarization.

DETAILED DESCRIPTION OF THE INVENTION

Figure 1:
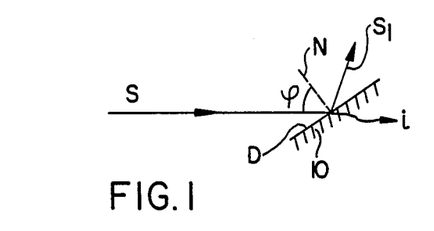
FIG. 1 is a schematic diagram of an exemplary embodiment of a photopolarimeter utilizing a polarization sensitive photodetector of the present invention.

As shown in FIG. 1, a photopolarimeter may be constructed from a single polarization sensitive photodetector 10 having a specularly reflecting surface D. A light beam S is incident upon the surface D at an oblique angle $\phi$ to the normal N of the detector 10. A portion S1 of the light is reflected from the surface D while the component of the incident radiation that is not reflected by the detector 10 is absorbed thereby. A proportional signal i is generated as a result of this absorption and is detected. By integrating the polarization-analysis and detection functions, we achieve a simple and novel polarimeter from which at least one parameter of the polarization of light can be determined.

Figure 2:
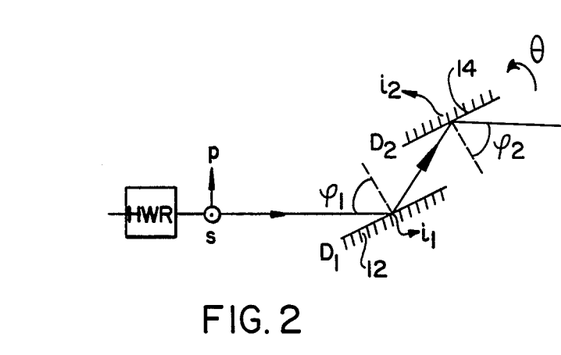
FIG. 2 is a schematic diagram of an exemplary embodiment utilizing two polarization-sensitive photodetectors.

FIG. 2 shows another embodiment including two polarization sensitive photodetectors 12 and 14 each having a partially specularly reflecting surface D1 and D2. Ideally, the detector surfaces D1 and D2 are parallel and they also function as a pair of crossed thin film reflection polarizers; however, this is not essential.

All of the incident radiation is captured by the two detectors 12, 14 and each detector generates an output electrical signal, $i_1$ and $i_2$, proportional to the fraction of radiation it absorbs. For simplicity we assumed the following ideal (power) reflectances of the detector surfaces for incident p- and s- polarized light:

$$R_{p1}=0, R_{s1}=1, \quad (1)$$

$$R_{s2}=0. \quad (2)$$

Equations (1) and (2) indicate that the surface of $D_1$ acts as an ideal reflection polarizer and that the surface of $D_2$ is antireflection-coated for the s-polarized light reflected by $D_1$.

In general, we denote by $I_p$ and $I_s$ the component fluxes (powers) of incident light that are polarized parallel (p) and perpendicular (s) to the common plane of incidence for the two reflections at $D_1$ and $D_2$. $I_1$ and $I_2$ are the fluxes absorbed by $D_1$ and $D_2$ which produce output electrical signals $i_1$ and $i_2$, respectively. Linear photodetection is assumed so that $$i_1=k_1I_1, i_2=k_2I_2, \quad (3)$$

where $k_1$ and $k_2$ are sensitivity constants characteristic of $D_1$ and $D_2$, respectively, and include any postdetection amplification factors.

When the ideal conditions of Eqs. (1) and (2) are satisfied, $I_1=I_p$ and $I_2=I_s$. Furthermore, if $k_1=k_2$ (i.e., the detector sensitivities are equal or equalized), the degree of linear polarization of incident light, which is defined by $$P=(I_p-I_s)/(I_p+I_s), \quad (4)$$

is obtained from the output signals of the photodetectors by $$P=(i_1-i_2)/(i_1+i_2). \quad (5)$$

Equation (5) indicates that, with such an arrangement, we have perhaps realized the simplest possible instrument for measuring the degree of linear polarization of light.

For Si photodetectors, null reflectances, $R_{pl}=0$ and $R_{s2}=0$ can be readily achieved by single-layer coatings at a given wavelength. For example, at $\lambda=632.8$ nm (of the often-used He-Ne laser), $R_{pl}<10^{-5}$ at the pseudo-Brewster angle, $\phi=75.44°$, of bare Si with complex refractive index 3.85-j0.02. In this case $R_{s1}=0.76$ and the second of Eqs. (1) is not satisfied. To make $R_{s2}=0$ at the same angle (parallel detector surfaces), the Si surface of $D_2$ is coated with a transparent layer of refractive index 1.37 (e.g., $MgF_2$) and of quarter-wave optical thickness (163.2 nm actual thickness). A protective layer of half-wave optical thickness of the same (or of different, e.g., $SiO_2$) dielectric can be applied to $D_1$, without affecting the condition $R_{p1}=0$. Multilayer coatings are required to satisfy all of Eqs. (1) and (2), at least approximately, over the useful spectral bandwidth of the photodetectors.

It is not essential that the two detector surfaces be parallel or that they should function as a pair of crossed polarizers, desirable as these conditions may be. However we will continue to assume a common plane of incidence for light reflections at the surfaces of the two detectors $D_1$ and $D_2$. In terms of $R_{p1}$, $R_{s1}$ and $R_{p2}$, $R_{s2}$, the p and s reflectances of $D_1$ and $D_2$, respectively, the detected signals are given by $$i_1=k_1[(1-R_{p1})I_p+(1-R_{s1})I_s],$$

$$i_2=k_2[(1-R_{p2})R_{p1}I_p+(1-R_{s2})R_{s1}I_s]. \quad (6)$$

In Eqs. (6), $I_p$ and $I_s$ are the component fluxes of incident light that are p and s polarized, and $k_1$ and $k_2$ are the photodetection sensitivity constants of $D_1$ and $D_2$, respectively, as has already been indicated. Equations (6) can be written in matrix form:

$$\begin{bmatrix} i_1 \\ i_2 \end{bmatrix} = \begin{bmatrix} a_{11} & a_{12} \\ a_{21} & a_{22} \end{bmatrix} \begin{bmatrix} I_p \\ I_s \end{bmatrix} \quad (7)$$

where $$a_{11}=k_1(1-R_{p1}), a_{12}=k_1(1-R_{s1}),$$

$$a_{21}=k_2R_{p1}(1-R_{p2}), a_{22}=k_2R_{s1}(1-R_{s2}). \quad (8)$$

Put more concisely, Eq. (7) reads $$\bar{i}=\bar{a}\,\bar{I}, \quad (9)$$

where $\bar{i}=(i_1i_2)^t$ is the signal vector, $\bar{I}=(I_pI_s)^t$ is the flux vector (where t indicates the transpose), and $\bar{a}=(a_{ij})$ is the 2×2 instrument matrix characteristic of the two photodetectors. From Eq. (9), $$\bar{I}=\bar{a}^{-1}\bar{i}, \quad (10)$$

which indicates that the input flux vector $\bar{I}$ is obtained by premultiplying the output signal vector $\bar{i}$ with the inverse of the instrument matrix $\bar{a}^{-1}$.

Unambiguous determination of $\bar{I}$ from Eq. (10) requires that $\bar{a}^{-1}$ exists, i.e., $\bar{a}$ must be nonsingular. In turn, $\bar{a}$ is nonsingular when its determinant is not zero, i.e.

$$\det \bar{a} \neq 0. \quad (11)$$

From Eqs. (8) we get $$\det \bar{a} = a_{11}a_{22} - a_{12}a_{21} \quad (12)$$

$$= k_1k_2[R_{s1}(1-R_{p1})(1-R_{s2}) - R_{p1}(1-R_{s1})(1-R_{p2})].$$

It is instructive to consider some special cases as examples. Let us assume identical detectors and drop the subscripts 1 and 2 from Eq. (12); we obtain $$\det \bar{a}=k^2(R_s-R_p)(1-R_s)(1-R_p). \quad (13)$$

Apart from the trivially obvious requirement that $k \neq 0$, Eq. (13) shows that the only essential condition for $\bar{a}$ to be nonsingular is that $$R_p \neq R_s \neq 1. \quad (14)$$

A particularly simple form of the determinant is obtained if we further assume incidence at 45° on uncoated detector surfaces; in this case $R_p=R_s^2$, and Eq. (13) reduces to $$det\ \bar{a}=k^2\ R_s(1+R_s)(1-R_s)^3. \tag{15}$$

For Si with the refractive index $3.85-j0.02$ at $\lambda=632.8$ nm, $R_s=0.47$ at 45° incidence, and $det\ \bar{a}=0.1k^2$, from Eq. (15).

Consider also the case of parallel Si detector surfaces that are coated such that $R_{p1}=0$, $R_{s1}=0.76$, $R_{s2}=0$ at the same angle of incidence $\phi=75.44°$ and $\lambda=632.8$ nm. Here $a_{ij}$ of Eqs. (8) simplify to $$\begin{array}{ll} a_{11} = k_1, & a_{12} = 0.24\ k_1, \\ a_{21} = 0, & a_{22} = 0.76\ k_2, \end{array} \tag{16}$$

and $$det\ \bar{a} = 0.76\ k_1 k_2. \tag{17}$$

As a final example, consider the arrangement obtained when the second detector surface is set to intercept normally (and totally absorb, using an antireflection coating) the light beam reflected from the first detector. In this case $a_{11}$ and $a_{12}$ of Eqs. (8) remain unchanged but $a_{21}$ and $a_{22}$ become $$a_{21}=k_2 R_{p1},\ a_{22}=k_2 R_{s1} \tag{18}$$

The determinant of $\bar{a}$ reduces to $$det\ \bar{a}=k_1 k_2(R_{s1}-R_{p1}), \tag{19}$$

which is nonzero provided that $k_1 k_2 \neq 0$ and $R_{s1} \neq R_{p1}$. For Si detectors at $\lambda=632.8$ nm, incidence at 75.44° on the first surface, which is uncoated or coated with a transparent protective dielectric layer of half-wave optical thickness, makes $R_{p1}=0$, $R_{s1}=0.76$, and $det\ \bar{a}=0.76 k_1 k_2$. The second surface can be antireflection-coated at normal incidence using a $Si_3N_4$ film of refractive index 1.9622 and of 80.4 nm thickness.

Once the input flux vector $\bar{I}$ is obtained from Eq. (10), the degree of linear polarization of the incident light P can be determined from Eq. (4).

Figure 3:
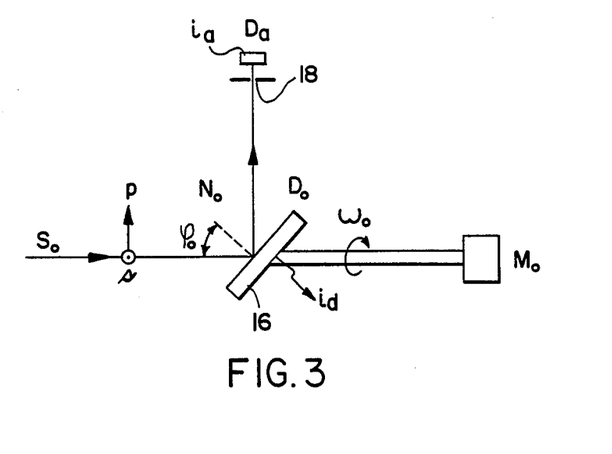
FIG. 3 is an exemplary embodiment of a rotating ellipsometer constructed according to the present invention.

FIG. 3 shows a unique ellipsometer that uses only a photodetector 16 and dispenses of all other optical elements. The detector surface Do is partially specularly reflecting and is set to intercept the incoming light beam So at an oblique angle of incidence $\phi_0$. Only a fraction of the incident radiation is absorbed which depends on the incident polarization and the azimuthal orientation of the plane of incidence (POI). The detector is synchronously rotated around the light beam as an axis. The surface normal No precesses in a conical fashion and the POI becomes a revolving plane through and around the incident beam. The output electrical signal $i_d$ of the photodetector, which is proportional to the fraction of radiation it absorbs, is modulated by the rotation. It is this modulation that determines the input state of polarization.

FIG. 3 is a schematic diagram of this simple rotating-detector ellipsometer (RODE). The detector $D_0$ is mounted, in a tilted orientation, on the shaft of a small synchronous motor M that rotates at an angular speed $\omega_0$. The light beam So, whose state of polarization is to be measured, strikes the specularly reflecting detector surface Do at an angle of oblique incidence $\psi_0$. The absorbed radiation generates the output electrical signal $i_d$. p and s denote the orthogonal linear polarization directions parallel p and perpendicular s to the plane of incidence (the plane of the page in FIG. 3).

A fixed reference plane, with respect to which the azimuth of the major axis of the polarization ellipse is determined, is established by a small aperture 18 and an auxiliary detector $D_a$ that is placed to intercept the (conically) rotating reflected beam. The output signal $i_a$ of $D_a$ provides a reference timing pulse that permits the determination of the azimuth of the polarization ellipse from the phase angle of the ac component of $i_d$. It is also possible to use an array of photodetectors, positioned behind a uniformly angularly spaced array of holes or slits around the circumference of a circle traced by the reflected light beam, as an angular encoding scheme for the digital sampling of the detected signal $i_d$.

Figure 4:
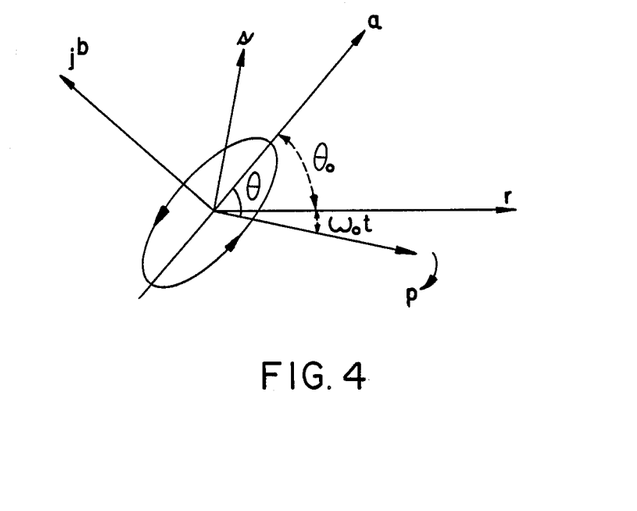
FIG. 4 is a diagram illustrating the ellipse of polarization taken from FIG. 3.

With reference to FIG. 4 let a and jb, where a and b are real and $j=\sqrt{-1}$, be the phasor components of the electric vector of incident totally polarized light along the major and minor axes of the polarization ellipse. The orthogonal directions p and s (parallel and perpendicular to the plane of incidence) rotate with the rotation of the detector at the angular speed $\omega_0$, and $\theta$ is the instantaneous azimuth between the major axis of the ellipse and the rotating p axis. The p and s phasor components of the electric vector are obtained by simple projection as $$E_p=a\ cos\theta-jb\ sin\theta,$$

$$E_s=a\ sin\theta+jb\ cos\theta. \tag{21}$$

Apart from a multiplicative constant, the corresponding p- and s- polarized component fluxes of incident light are $$I_p=E^*_p\ E_p=\frac{1}{2}I_0(1+cos2\epsilon cos2\theta),$$

$$I_s=E^*_s\ E_s=\frac{1}{2}I_0(1-cos2\epsilon cos2\theta), \tag{21}$$

where $$I_0 = I_p + I_s \tag{22a}$$

$$= a^2 + b^2,$$

$$cos2\epsilon = (a^2 - b^2)/(a^2 + b^2). \tag{22b}$$

$\epsilon=tan^{-1}(b/a)$ is the ellipticity angle which falls in the range $-45°\leq\epsilon\leq45°$; the limiting values of $\epsilon=-45°$ and $\epsilon=+45°$ represent left- and right-handed circularly polarized light, respectively. The light flux absorbed by the photodetector is given by $$I_d=(1-R_p)I_p+(1-R_s)I_s, \tag{23}$$

where $R_p$ and $R_s$ are the (power) reflectances of the detector surface for incident p- and s- polarized light. We assume linear photodetection, so that the output electrical signal of the detector is $$i_d=k\ I_d, \tag{24}$$

where the sensitivity constant k is independent of $I_d$ but may vary with wavelength. Substitution of Eqs. (21) and (22a) into Eq. (23), and using the result into Eq. (24), yield the simplified expression $$i_d=i_0(1+m\ cos2\theta), \tag{25}$$

where $$i_0 = k I_0(1-R_u), \quad (26)$$

$$R_u = \tfrac{1}{2}(R_p + R_s), \quad (27)$$

$$m = m_L \cos 2\epsilon, \quad (28)$$

$$m_L = (R_s - R_p)/(2 - R_s - R_p). \quad (29)$$

$R_u$ of Eq. (27) is the detector surface reflectance for inicident unpolarized or circularly polarized light. In Eq. (25) m represents the modulation depth of the detected signal (ratio of amplitudes of the ac and dc components of the signal) that results from rotation of the detector. Equation (28) indicates that when $\epsilon = 0$, $m = m_L$; i.e. $m_L$ is the modulation depth obtained when the incident light is linearly polarized.

Figure 5:
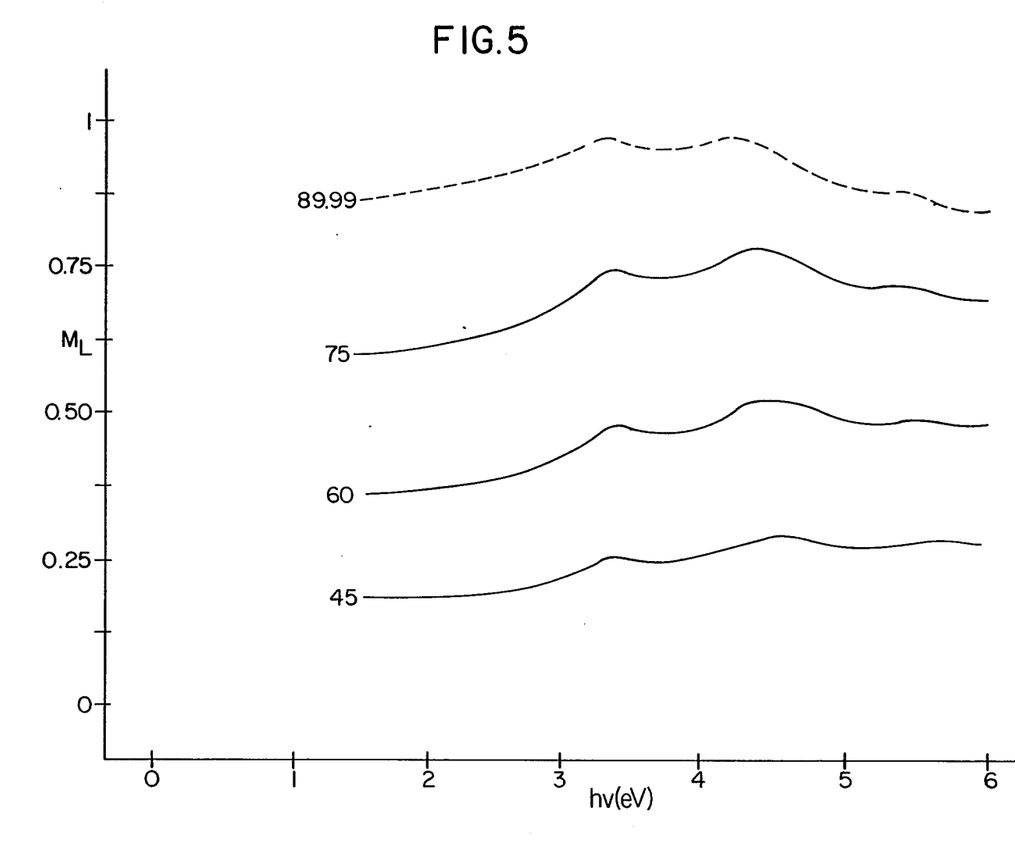
FIG. 5 is a graph illustrating the modulation depth of the detected signal for incident linearly polarized light versus the photon energy at different angles of incidence.

Equation (29) tells us that $m_L$ is also a property of the detector surface at a given angle of incidence and wavelength. In FIG. 5 $m_L$, computed from Eq. (29), is plotted as a function of photon energy between 1.5 and 6 eV for an uncoated Si surface using known optical constants, at three angles of incidence $\phi = 45, 60$ and $75°$. At a given $\phi$, $m_L$ changes within a narrow range; e.g. at $\phi = 60°$, $0.355 < m_L \, 0.519$. Furthermore, $m_L$ increases as $\phi$ increases and approaches 1 as $\phi \to 90°$ (broken curve).

$m_L$ can be determined by calibration, once and for all, for a given detector at a given angle of incidence by recording the modulation depth of the detected signal as a function of wavelength with a (broad-band, very-low-extinction-ratio) linear polarizer placed in the path of the light beam.

When incident light of unknown polarization shines on the rotating photodetector, the resulting measured modulation depth m determines the ellipticity angle by $$\cos 2\epsilon = m/m_L, \quad (30)$$

from Eq. (28), where $m_L$ is now considered known. The sign of $\epsilon$ is indeterminate and RODE is handedness blind, similar to known rotating-analyzer elliptometers.

The instantaneous azimuth $\theta$ that appears in Eqs. (20), (21) and (25) can be written as $$\theta = \theta_0 + \omega_0 t, \quad (31)$$

where $\theta_0$ is the desired major-axis azimuth of the polarization ellipse measured from the fixed reference plane (the reference direction r in FIG. 4). Substitution of Eq. (31) into Eq. (25) gives $$i_d = i_0[1 + m \cos(2\omega_0 t + 2\theta_0)]. \quad (32)$$

Equation (32) shows that the azimuth angle $\theta_0$ is determined by the phase angle of the ac component of the detected signal $i_d$ whose frequency is double the rotational frequency of the detector. The timing pulse from the auxiliary detector $D_a$ in FIG. 3 defines the time $t = 0$, or the beginning of a period (of duration $\pi/\omega$) of the periodic signal $i_d$ of Eq. (32).

The advantages of RODE are summarized below.

(1) RODE is the simplest possible ellipsometer because it has the least number of optical components, only one—the photodetector itself, for polarization measurement.

(2) RODE is suited for spectroscopic ellipsometry because its spectral range is limited only by available photodetectors, and not by any other polarizing optical elements.

(3) Timing pulses, essential for absolute azimuth measurement and analog-to-digital conversion of the detected signal, are readily available by intercepting the rotating reflected beam by an array of auxiliary detectors arranged around a circle.

(4) A simple calibration procedure permits the direct determination of ellipticity angle from the modulation depth of the detected signal.

(5) The sensitivity of the ellipsometer can be conveniently controlled by adjusting the angle of incidence $\phi_0$. Dielectric-layer coatings can also be applied to the detector surface to alter its reflectance characteristics and achieve optimal performance over certain spectral ranges.

Alternatively, to measure the ellipse (state) of polarization of incident totally polarized light, except for handedness, the two-detector system of FIG. 2 is rotated as one unit around the incident beam by a prespecified angle $\theta$ and the measurement of P is repeated. To maintain a common plane of incidence for the two reflections independent of the rotation of the detector assembly, and retain mechanical simplicity, the detector surfaces should be parallel.

The input state of polarization is represented concisely by the complex polarization number $$X = E_s/E_p = \tan\psi \exp(j\Delta), \quad (33)$$

where $E_p$ and $E_s$ are the phasor components of the electric vector of light parallel and perpendicular to the plane of incidence, respectively, in the reference orientation $\theta = 0$. The degree of linear polarization P is related to X by $$P = (1 - XX^*)/(1 + XX^*), \quad (34)$$

hence $$P = \cos 2\psi, \quad (35)$$

if Eq. (33) is used. Rotation of the detector assembly rotates the plane of incidence by the angle $\theta$. A convenient choice of $\theta = 45°$ transforms X to X' where $$X' = (X - 1)/(X + 1). \quad (36)$$

From Eqs. (33), (34) and (35), the degree of polarization P' in the new $\theta = 45°$ orientation is given by $$P' = \sin 2\psi \cos \Delta. \quad (37)$$

According to Eqs. (35) and (37), measurements of P and P' determine the polarization parameters $\psi$ and $\Delta$ simply, directly, and completely. Notice, however, that it is $\cos \Delta$ that is determined. Consequently the sign of $\Delta$, hence the handedness of the incident polarization, remains ambiguous. The situation is identical to that encountered in the rotating-analyzer ellipsometer.

A calibrated scale for the detector rotation is not necessary. Only pinned rotational positions at $\theta = 0$ (reference), $\theta = 45°$, and $\theta = 90°$ are needed. Mechanical rotation can be altogether avoided if a half-wave retarder (HWR) is inserted in the incident beam to achieve an equivalent rotation of the plane of incidence. The half-wave retardation can be electro-optically or piezo-optically induced so that an ellipsometer with no moving parts is obtained. It should be noted that the degree of linear polarization P of incident totally or partially polarized light is of its own important in several applications, such as in atmospheric optics and in linear-dichroism measurements, and it can be measured fast by the two-detector ellipsometer (TDE) in the $\theta = 0$ orientation.

The instrument matrix $\bar{a}$ can be calculated from the known characteristics of the two detectors using Eqs. (8). However, a more practical approach is to determine $\bar{a}$ by calibration. $\bar{a}$ is a function of wavelength and must be measured over the useful spectral bandwidth of the detectors. A light source-monochromator combination produces a collimated monochromatic light beam which is linearly polarized by passing it through a good (crystal) polarizer. The detector assembly is set in the $\theta = 0$ reference orientation and the polarizer is rotated until the transmitted electric vector is parallel (p) and to the plane of incidence. The input flux vector becomes $\bar{I} = (I_c 0)^t$. The output signals of the two photodetectors, denoted by $i_{1pc}$ and $i_{2pc}$, are recorded as functions of wavelength $\lambda$. (At a given $\lambda$, $i_{1pc}$ is the maximum output signal of uncoated, or very-thin-film-coated, detector that is obtained when the polarizer is rotationally adjusted to its proper azimuth.)

With the polarizer fixed, the detector assembly is rotated to its $\theta = 90°$ position. The input light is now s polarized, with flux vector $\bar{I} = (0\ I_c)^t$, and the induced output signals $i_{1sc}$ and $i_{2sc}$ of the two photodetectors are again recorded. (The flux of light leaving the polarizer $I_c$ is the same in the $\theta = 0$ and $90°$ calibration steps if a stable source is used, but $I_c$ may vary with $\lambda$.) The four calibration signals $i_{1pc}$, $i_{2pc}$, $i_{1sc}$ and $i_{2sc}$ are sufficient to determine the instrument matrix $\bar{a}$ through Eq. (7); the result is $$\bar{a}(\lambda) = \frac{1}{I_c(\lambda)} \begin{bmatrix} i_{1pc}(\lambda) & i_{1sc}(\lambda) \\ i_{2pc}(\lambda) & i_{2sc}(\lambda) \end{bmatrix}, \quad (38)$$

where the argument $\lambda$ has been added to emphasize the wavelength dependence of the various quantities. $I_c(\lambda)$ need not be measured and no absolute photometry is required. To determine P requires only that $\bar{a}$ be determined up to a constant scalar multiplier. Therefore, the $1/I_c(\lambda)$ term in Eq (38) can be ignored.

Calibration of a given TDE need only be carried out once, and the instrument matrix $\bar{a}$ is stored for all subsequent polarization measurements. The TDE can be interfaced with an on-line microcomputer which accepts as input the digitized (sampled) output signals of the two photodetectors and produces the desired polarization parameters of the incident light as output.

This type of instrument is particularly useful for polarization-state measurements in the vacuum ultraviolet, where conventional transmission optics are not usable. In this spectral range the photons are energetic enough to eject electrons from the mirror surfaces, and these electron currents can be amplified by suitable dynode structures.

Figure 6:
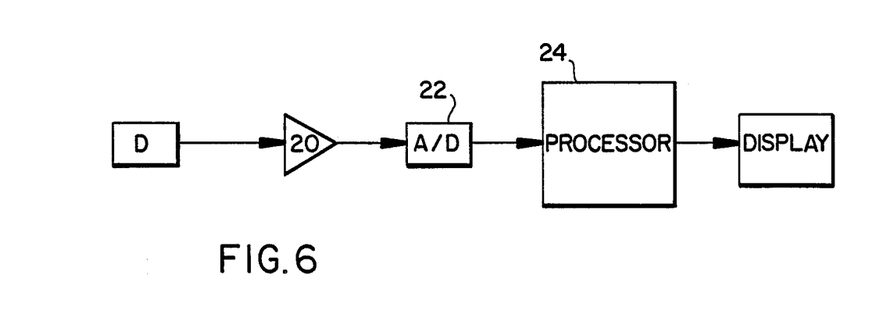
FIG. 6 is a block diagram illustrating the connection of a polarization sensitive photodetector to a signal processing arrangement.

FIG. 6 is a block diagram of an exemplary signal processing arrangement in which the output signals of one or more photodetectors D are initially amplified at 20, and are then converted to digital equivalent values by analog to digital converters 22 which are directed as inputs to a processor 24, preferably a microprocessor, which performs the necessary calculations. In an alternative embodiment, the processor 24 may be equipped to handle the A/D conversions.

As shown in FIG. 6, any of the instruments of FIGS. 1, 2 or 3 can be readily interfaced to an on-line microcomputer 24 which receives as its input the digitized output electrical signals. The microcomputer determines the the state of polarization of the light beam. In use with the ellipsometers described above, the microcomputer 24 may have stored in memory to determine the state of polarization. The result can be displayed on a suitable output device 26.

While several embodiments and variations of the for a photodetector arrangement for measuring the state of polarization of light are described in detail herein, it should be apparent that the disclosure and teachings of the present invention will suggest many alternative designs to those skilled in the art.

What is claimed is:

1. An apparatus for the measurement of at least one parameter of the state of polarization of a light beam comprising: at least one polarization sensitive photodetector having a partially specularly reflecting surface on which the light beam is incident such that a component of the light beam is reflected and a component of the light beam is absorbed by the photodetector, said polarization sensitive photodetector producing an electrical output signal having a magnitude proportional to the radiation absorbed by the photodetector from which at least one parameter of the state of polarization may be determined.

2. The apparatus of claim 1 wherein the photodetector is positioned to intercept the light beam at an oblique angle of incidence.

3. The apparatus of claim 1 further including means for determining at least one parameter of the state of polarization of the light beam from said electrical output signal.

4. The apparatus of claim 1 further including means for rotating said at least one photodetector around an axis defined by the incident light beam.

5. The apparatus of claim 1 wherein there are two of said polarization sensitive photodetectors such that;
   (a) a first of said photodetectors partially reflects the light beam incident thereon and produces a first electrical output signal having a magnitude proportional to the radiation absorbed by the first photodetector; and
   (b) a second of said photodetector being positioned so that the light beam partially reflected from the first photodetector is incident on said second photodetector and produces a second electrical output signal having a magnitude proportional to the radiation absorbed by the second photodetector.

6. The apparatus of claim 3 wherein said means for determining the at least one parameter of the state of polarization includes a microcomputer.

7. An ellipsometer for measuring the state of polarization of a light beam comprising:
   (a) a photodetector having a partially specularly reflecting surface on which the light beam is incident at an oblique angle with a plane of incidence and is partially reflected therefrom, said photodetector producing an electrical output signal having a magnitude proportional to the radiation absorbed by the photodetector; and
   (b) means coupled to said photodetector for rotating said photodetector around an axis defined by the incident light beam to modulate the electrical output signal.

8. The ellipsometer of claim 7 wherein said rotating means includes a synchronous or stepping motor.

9. The ellipsometer of claim 7 further including means coupled to said modulated electrical output signal for determining the state of polarization of a light beam.

10. The ellipsometer of claim 7 wherein said rotating means rotates the photodetector such that said photodetector precesses about an axis normal to said specularly reflecting surface whereby said light partially reflected therefrom is a conically rotating reflecting light beam.

11. The ellipsometer of claim 7 further including means for determining the azimuth angle of the plane of incidence of the light beam.

12. The ellipsometer of claim 11 wherein said means for determining the azimuth angle includes an auxiliary photodetector that intercepts the light beam reflected from said specularly reflecting photodetector, said auxiliary photodetector producing an auxiliary electrical output signal in the form of a timing pulse.

13. The ellipsometer of claim 12 further including a plurality of said auxiliary photodetectors positioned around said specularly reflecting photodetector to intercept the rotating reflected light beam at a plurality of angles to provide an angular encoding scheme for converting said modulated electrical output signals to corresponding digital signals.

14. The ellipsometer of claim 13 further including means coupled to receive said corresponding digital signals for calculating the elliptic polarization of a light beam.

15. The ellipsometer of claim 13 wherein said calculating mean is a microcomputer having calibration data obtained with a linearly polarized light beam stored therein.

16. The ellipsometer of claim 12 including means coupled to said modulated electrical output signal and said auxiliary output signal for determining the input state of polarization of a light beam with respect to a reference plane of incidence of the light beam.

17. The ellipsometer of claim 16 wherein said means for determining the input state of polarization includes a microcomputer having calibration data stored therein.

18. An apparatus for the measurement of at least one parameter of the state of polarization of a light beam comprising:
(a) a first photodetector having a partially specularly reflecting detecting surface on which the light beam is incident at an oblique angle and is partially reflected therefrom, said first photodetector producing a first electrical output signal having a magnitude proportional to the radiation absorbed by the first photodetector; and
(b) a second photodetector having a detecting surface on which the light beam partially reflected from the first photodetector is incident, said second photodetector producing a second electrical output signal having a magnitude proportional to the radiation absorbed by the second photodetector.

19. The apparatus of claim 18 wherein the light beam incident on the first photodetector and the partially reflected light beam incident on the second photodetector are incident at a common plane of incidence.

20. The apparatus of claim 19 wherein the detecting surface of said second detector is a partially specularly reflecting surface.

21. The apparatus of claim 20 wherein the partially reflected light beam is incident on said second photodetector at an oblique angle.

22. The apparatus of claim 19 wherein the detecting surface of said second detector is a substantially totally light absorptive surface.

23. The apparatus of claim 22 wherein the partially reflected light beam is incident on said second photodetector normal to the detecting surface of said second photodetector.

24. The apparatus of claim 20 or 22 wherein the detecting surface of said first and second photodetectors are parallel to each other.

25. The apparatus of claims 20 or 22 including means coupled to said first and second output signals for measuring the degree of linear polarization of the light beam.

26. The apparatus of claim 24 including means for rotating the first and second photodetector as an integral unit by a predetermined angle with respect to the light beam incident on the first photodetector, said first photodetector producing a third electrical output signal at the rotated position and the second photodetector producing a fourth electrical output signal at the rotated position.

27. The apparatus of claim 26 including means coupled to receive said first, second, third and fourth electrical output signals for determining the state of polarization of the light beam.

28. An ellipsometer for measuring the state of polarization of a light beam, comprising:
(a) a first photodetector having a partially specularly reflecting detecting surface in which the light beam is incident at an oblique angle with a first plane of incidence and is partially reflected therefrom, said first photodetector producing a first electrical output signal having a magnitude proportional to the radiation absorbed by the first photodetector;
(b) a second photodetector having a detecting surface on which the light beam partially reflected from the first photodetector is incident at a plane of incidence, substantially coincident with the first plane of incidence, said second photodetector producing a second electrical output signal having a magnitude proportional to the radiation absorbed by the second photodetector;
(c) means for rotating the plane of incidence of the light beam incident on the first photodetector to a second plane of incidence different from the first plane of incidence, said first photodetector producing a third electrical output signal at the second plane of incidence and the second photodetector producing a fourth electrical output signal at the second plane of incidence.

29. The ellipsometer of claim 28 wherein the detecting surface of said first and second photodetectors are parallel to each other.

30. The ellipsometer of claim 29 including means coupled to said first, second, third and fourth electrical output signals for measuring the polarization parameters $\psi$ and $\cos \Delta$.

31. The ellipsometer of claim 30 including means for storing calibration data to thereby determine the state of polarization of the light beam.

32. The ellipsometer of claim 28 wherein the detecting surface of said second detector is a partially specularly reflecting surface.

33. The apparatus of claim 28 wherein the partially reflected light beam is incident on said second photodetector at an oblique angle.

34. The apparatus of claim 28 wherein the detecting surface of said second detector is a substantially totally light absorptive surface.

35. The ellipsometer of claim 28 wherein said is provided by a half-wave retarder inserted within the light beam incident on the first photodetector.

36. The ellipsometer of claim 35 wherein said half-wave retarder is an electro-optical retarder.

37. The ellipsometer of claim 35 wherein said half-wave retarder is a piezo-optical retarder.

38. The ellipsometer of claim 28 wherein said rotating means includes a stepping motor.

39. A method for measuring at least one parameter of the state of polarization of a light beam, comprising:
(a) directing the light beam on to a photodetector having a partially specularly reflecting surface on which the light beam is incident,
(b) producing with said photodetector an electrical output signal having a magnitude proportional to the radiation absorbed by the photodetector,
(c) detecting said electrical output signal, and
(d) determining the at least one parameter of the state of polarization from said electrical output signal.

40. The method of claim 39 further including the step of rotating the photodetector around an axis defined by the incident light beam.

41. A method for measuring the elliptic polarization of a light beam comprising:
(a) directing the light beam onto a first photodetector having a first partially specularly reflecting surface on which the light beam is incident at an oblique angle, and producing an electrical output signal having a magnitude proportional to the radiation absorbed thereby;
(b) rotating said first photodetector around an axis defined by the incident light beam; and
(c) directing the light beam reflected from said first photodetector on to a second photodetector producing a second electrical output signal having a magnitude proportional to the radiation absorbed thereby.

42. A method for measuring the elliptic state of polarization of a light beam comprising:
(a) directing the light beam onto a first photodetector having a partially specularly reflecting detecting surface on which the light beam is incident at an oblique angle with a first plane of incidence and is partially reflected therefrom, and producing with said first photodetector a first electrical output signal having a magnitude proportional to the radiation absorbed thereby;
(b) directing the light beam partially reflected from the first photodetector on to a second photodetector at a plane of incidence substantially coincident with the first plane of incidence, and producing with said second photodetector a second electrical output signal having a magnitude proportional to the radiation absorbed thereby; and
(c) rotating the plane of incidence of the light beam incident on the first photodetector to a second plane of incidence different from the first plane of incidence, and producing with said first photodetector a third electrical output signal and producing with said second photodetector a fourth electrical output signal having a magnitude proportional to the radiation absorbed thereby.

* * * * *

UNITED STATES PATENT AND TRADEMARK OFFICE
CERTIFICATE OF CORRECTION

PATENT NO. : 4,725,145

DATED : February 16, 1988

INVENTOR(S) : Rasheed M. A. Azzam

It is certified that error appears in the above-identified patent and that said Letters Patent is hereby corrected as shown below:

Column 10, line 8: "variations of the for" should read as --variations of the present invention for--

Column 13, line 4, Claim 35: "wherein said is provided" should read as --wherein said rotating means is provided--

Signed and Sealed this

Eleventh Day of October, 1988

Attest:

DONALD J. QUIGG

Attesting Officer

Commissioner of Patents and Trademarks